United States Patent
Gao et al.

(10) Patent No.: US 11,259,770 B2
(45) Date of Patent: Mar. 1, 2022

(54) METHODS AND SYSTEMS FOR NOISE REDUCTION IN X-RAY IMAGING

(71) Applicant: GE Precision Healthcare LLC, Milwaukee, WI (US)

(72) Inventors: Feng Gao, Naperville, IL (US); Mahesh Narayanaswamy, Wauwatosa, WI (US)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 110 days.

(21) Appl. No.: 16/684,348

(22) Filed: Nov. 14, 2019

(65) Prior Publication Data
US 2021/0145393 A1 May 20, 2021

(51) Int. Cl.
*A61B 6/00* (2006.01)
*G06T 7/00* (2017.01)

(52) U.S. Cl.
CPC .......... *A61B 6/5258* (2013.01); *G06T 7/0012* (2013.01); *G06T 2207/10116* (2013.01); *G06T 2207/20084* (2013.01)

(58) Field of Classification Search
None
See application file for complete search history.

(56) References Cited

U.S. PATENT DOCUMENTS

| 7,649,979 | B2 * | 1/2010 | Liu | H04N 5/3577 378/98.11 |
| 8,517,145 | B2 * | 8/2013 | Omi | G06T 5/002 182/132 |
| 2018/0158177 | A1 * | 6/2018 | Lannes | G06K 9/36 |
| 2019/0104940 | A1 * | 4/2019 | Zhou | G06T 11/008 |

FOREIGN PATENT DOCUMENTS

| CN | 105427240 A | * | 3/2016 | |
| EP | 3451284 A1 | * | 3/2019 | ........... G06T 7/0012 |
| WO | WO-2017096758 A1 | * | 6/2017 | ............... G06K 9/46 |

OTHER PUBLICATIONS

Machine english translation of WO-2017096758-A1 (Year: 2017).*
Maching english translation of CN-105427240-A (Year: 2016).*
Machine translation of EP-3451284-A1 (Year: 2019).*

* cited by examiner

*Primary Examiner* — Vu Le
*Assistant Examiner* — Courtney Joan Nelson

(57) ABSTRACT

Various methods and systems are provided for x-ray imaging. In one embodiment, a method for an x-ray imaging system comprises acquiring, with an x-ray detector, an image including a noise artifact caused by electromagnetic interference, inputting the image to a trained neural network model to obtain a corrected image with the noise artifact removed, and outputting the corrected image. In this way, row-correlated noise artifacts caused by electromagnetic interference at the x-ray detector are eliminated or cancelled in real time and image quality is improved.

16 Claims, 7 Drawing Sheets

METHODS AND SYSTEMS FOR NOISE REDUCTION IN X-RAY IMAGING

FIELD

Embodiments of the subject matter disclosed herein relate to x-ray imaging.

BACKGROUND

Digital x-ray imaging systems are becoming increasingly widespread for producing digital data which can be reconstructed into useful radiographic images. In current digital x-ray imaging systems, radiation from a source is directed toward a subject, typically a patient in a medical diagnostic application. A portion of the detector converts the radiation to light photons that are sensed. The detector is divided into a matrix of discrete picture elements or pixels, and encodes output signals based upon the quantity or intensity of the radiation impacting each pixel region. The detector communicates the encoded output signals to a host computer, which processes the image received based on the digital pixel values. The resulting radiographic image shows internal portions of the imaged subject.

BRIEF DESCRIPTION

In one embodiment, a method for an x-ray imaging system comprises acquiring, with an x-ray detector, an image including a noise artifact caused by electromagnetic interference, inputting the image to a trained neural network model to obtain a corrected image with the noise artifact removed, and outputting the corrected image. In this way, row-correlated noise artifacts caused by electromagnetic interference at the x-ray detector are eliminated or cancelled in real time and image quality is improved.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
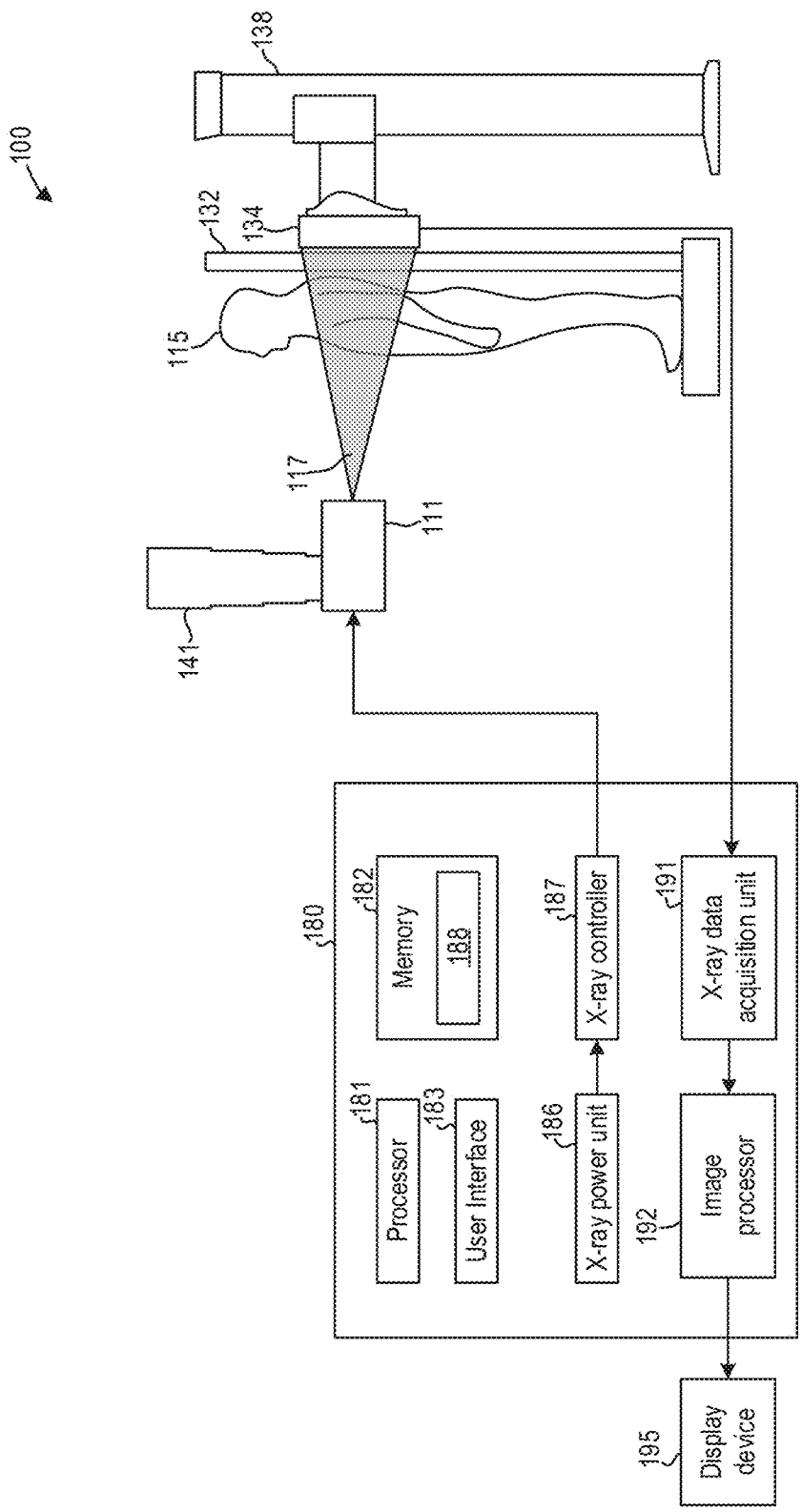
FIG. 1 shows an example x-ray imaging system according to an embodiment.
Figure 2:
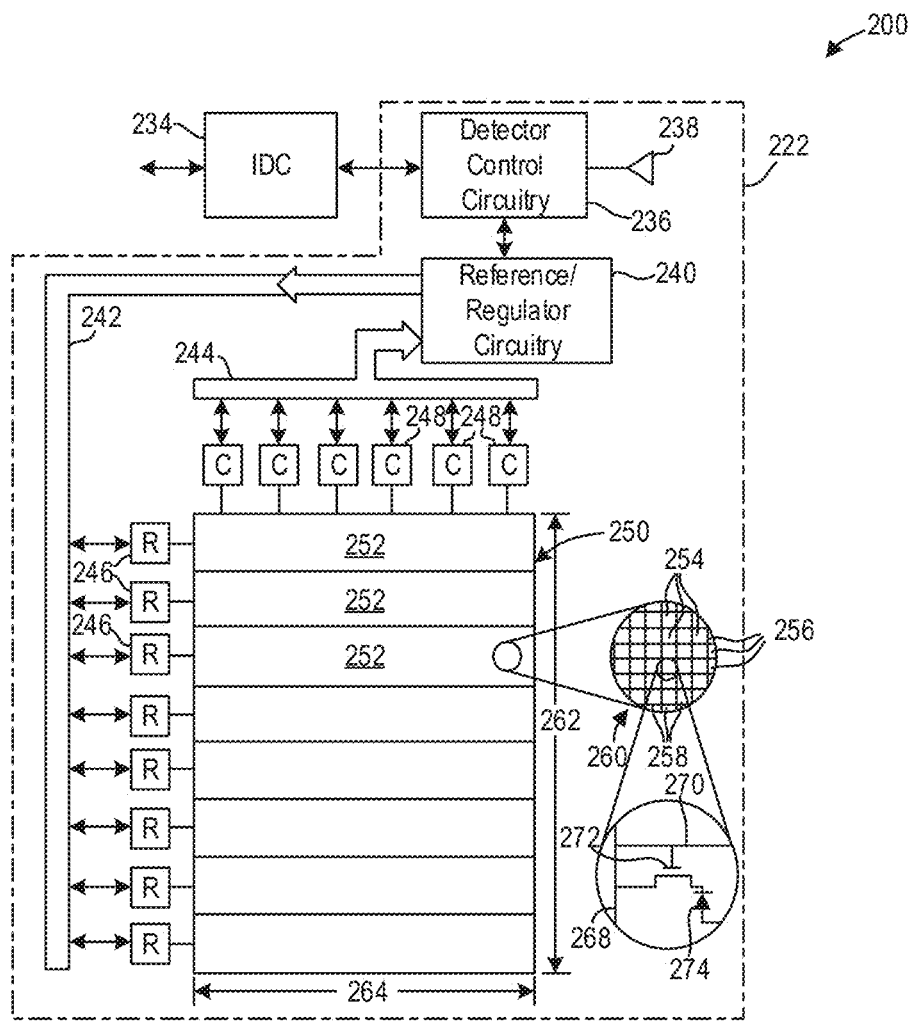
FIG. 2 shows a diagram illustrating example functional circuitry that may be included in a detector of the x-ray imaging system of FIG. 1 according to an embodiment.
Figure 3:
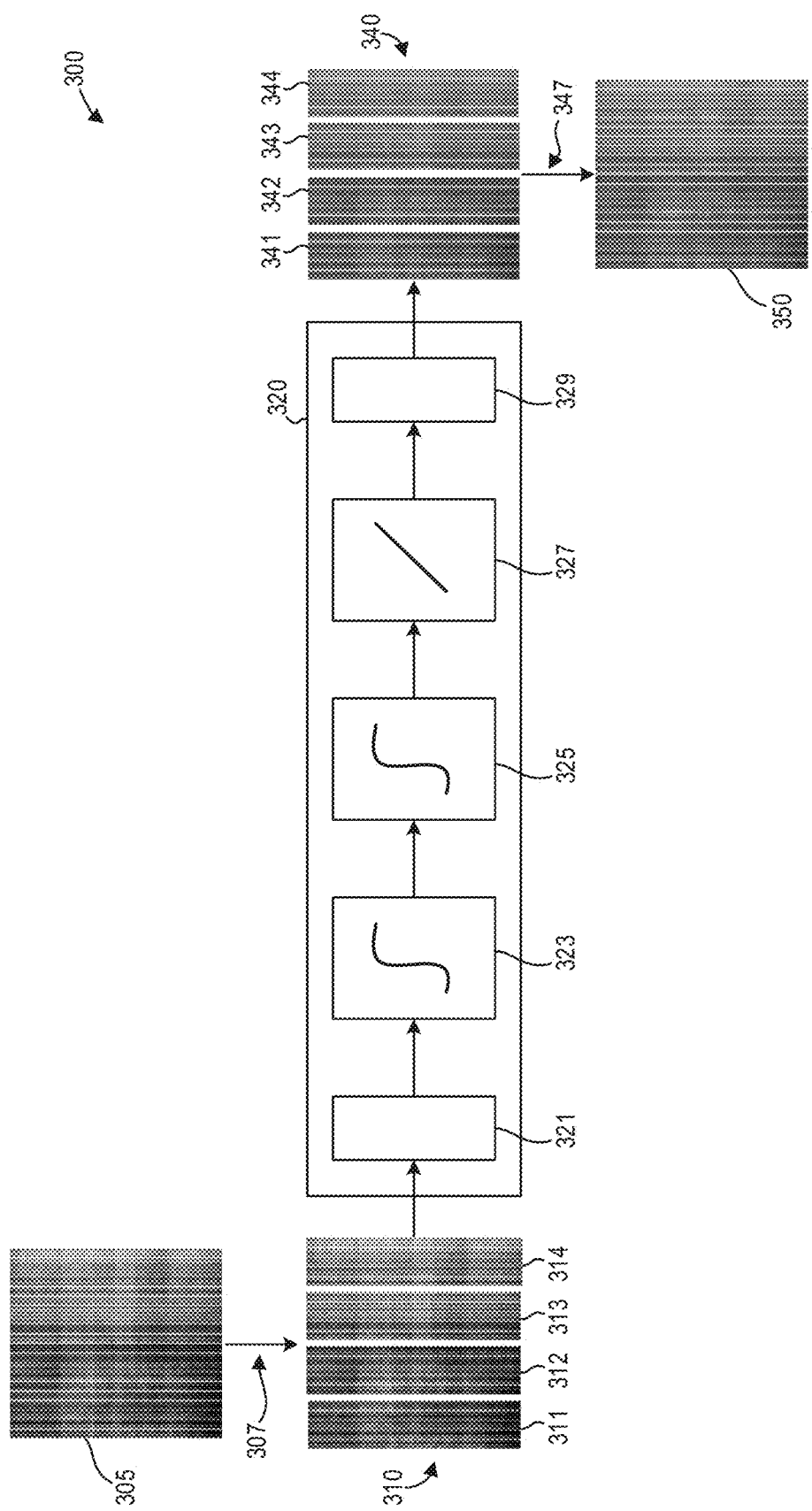
FIG. 3 shows a high-level diagram illustrating an example neural network model for reducing image noise according to an embodiment.
Figure 4:
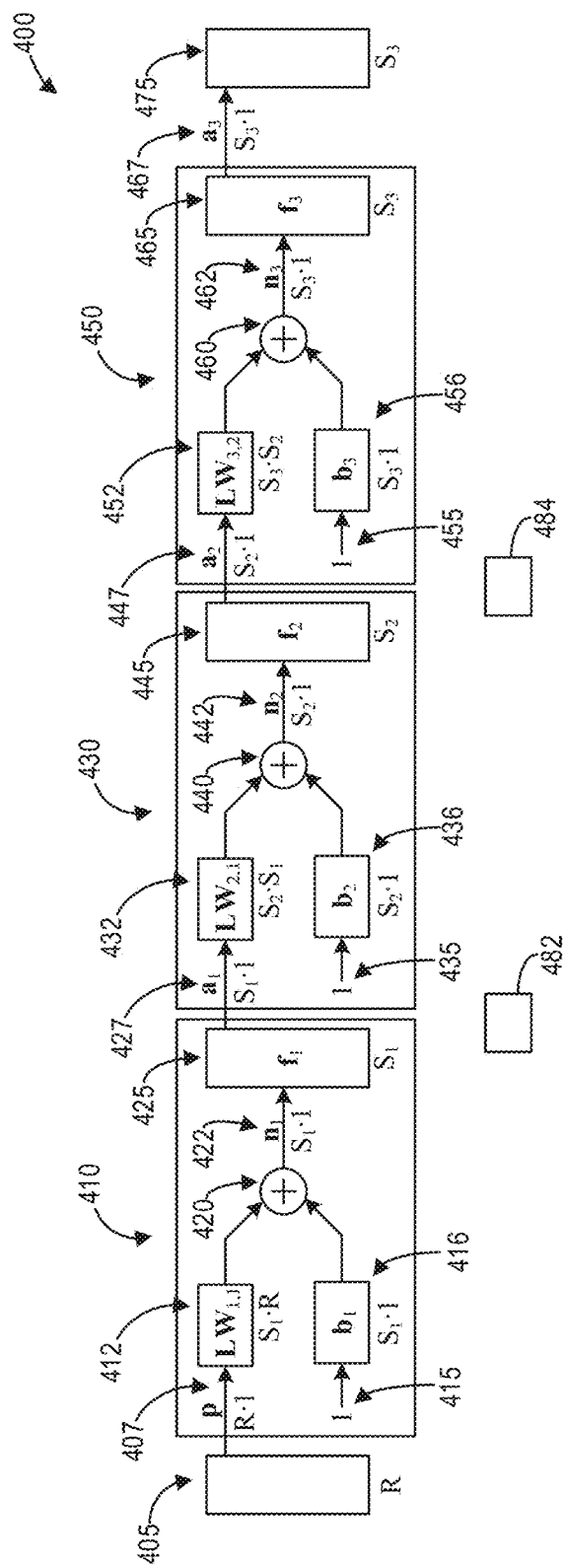
FIG. 4 shows a high-level diagram illustrating an example architecture for the neural network model of FIG. 3 according to an embodiment.

The following description relates to various embodiments of x-ray imaging. In particular, systems and methods for reducing noise artifacts in x-ray images caused by electromagnetic interference (EMI) are provided. The use of digital x-ray detectors in x-ray imaging systems, such as the x-ray imaging system shown in FIG. 1, is becoming ubiquitous and gradually replacing the use of the film cassette for acquiring x-ray images. While digital x-ray detectors provide substantial advantages over film cassettes with regard to image quality, processing time, storage, and image transfer, such detectors are also subject to electromagnetic interference. In particular, digital x-ray detectors, as shown in FIG. 2, include a large number of scan lines or rows to provide increased sensitivity and thereby enable reduced x-ray dose exposure for patients. However, electromagnetic interference in turn produces a large amount of noise at these scan lines, with a noise frequency that is usually associated with the row spatial distribution and external electromagnetic sources. Typical attempts to mitigate the effect of EMI on digital x-ray detectors includes providing additional physical shielding to electromagnetic sources within the x-ray imaging system. However, such approaches increase the cost and complexity of the system, and furthermore are not a particularly effective way to prevent EMI noise. In embodiments disclosed herein, a neural network model, such as the neural network model depicted in FIGS. 3 and 4, is trained with pairs of noisy images and clean, target images, such as the pair of images depicted in FIG. 5, such that the neural network model accepts an image with EMI noise as input and outputs the image with the EMI noise substantially reduced. As depicted in FIG. 6, such a neural network model is particularly effective at eliminating image noise artifacts caused by EMI. A method for training such a neural network model, such as the method depicted in FIG. 7, includes sub-dividing each noisy input image into a plurality of images to increase the training base and reduce the training time. Further, by slicing each image into quarters or another number of segments along the direction perpendicular to the scan lines, the noise reduction is improved and the neural network model converges faster. When the neural network is deployed, an acquired image may be similarly sub-divided prior to input to the trained neural network model, as depicted in FIG. 8, and then the sub-images output by the neural network model are stitched or combined back together to generate the corrected image without EMI noise.

Turning now to FIG. 1, a block diagram of an x-ray imaging system 100 in accordance with an embodiment is shown. The x-ray imaging system 100 includes an x-ray source 111 which radiates x-rays 117, a stand 132 upon which the subject 115 stands during an examination, and an x-ray detector 134 for detecting the x-rays 117 radiated by the x-ray source 111 and attenuated by the subject 115. The x-ray detector 134 may comprise, as non-limiting examples, a scintillator, one or more ion chamber(s), a light detector array, an x-ray exposure monitor, an electric substrate, and so on. The x-ray detector 134 is mounted on a stand 138 and is configured so as to be vertically moveable according to an imaged region of the subject. It should be appreciated that in some examples, the x-ray imaging system 100 may include a table (not shown) instead of the stand 138, such that the subject 115 may be positioned on the table during imaging.

The operation console 180 comprises a processor 181, a memory 182 storing executable instructions 188, a user interface 183 for enabling user input, an x-ray power unit 186, an x-ray controller 187, an x-ray data acquisition unit 191, and an image processor 192. The user interface 183, which may comprise one or more of a keyboard, a mouse, a touchscreen device, a trackpad, one or more switches, one or more buttons, and so on, enables a user of the x-ray imaging system 100 to provide user input to control one or more elements of the x-ray imaging system 100. X-ray image data transmitted from the x-ray detector 134 is received by the x-ray data acquisition unit 191. The collected x-ray image data are image processed by the image processor 192. A display device 195 communicatively coupled to the operating console 180 displays an image-processed x-ray image thereon.

The x-ray source 111 is supported by a support post 141 which may be mounted to a ceiling (e.g., as depicted) or mounted on a moveable stand for positioning within an imaging room. The x-ray source 111 is vertically moveable relative to the subject or patient 115. For example, one or more motors (not shown) may be integrated into the support post 141 and may be configured to adjust a vertical position of the x-ray source 111 by increasing or decreasing the distance of the x-ray source 111 from the ceiling or floor, for example. To that end, the operation console 180 may include a motor drive (not shown) communicatively coupled to the one or more motors and configured to control the one or more motors.

The x-ray power unit 184 and the x-ray controller 182 supply power of a suitable voltage current to the x-ray source 111. A collimator (not shown) may be fixed to the x-ray source 111 for designating an irradiated field-of-view of an x-ray beam. The x-ray beam radiated from the x-ray source 111 is applied onto the subject via the collimator.

The x-ray detector 134 may comprise a digital x-ray detector such as a flat panel detector. Such an x-ray detector 134 is highly advantageous in comparison to previous x-ray detectors such as film cassettes, especially in terms of image quality, processing time, storage, image transfer, and x-ray dose exposure for patients.

As an illustrative and non-limiting example, FIG. 2 is a diagrammatical representation of an x-ray detection system 200 that depicts functional components of a digital x-ray detector 222, which may be implemented as the x-ray detector 134 in the x-ray imaging system 100. The x-ray detection system 200 also includes an imaging detector controller (IDC) 234, which may be configured within a detector controller or x-ray data acquisition unit 191, for example. IDC 234 includes a CPU or digital signal processor, as non-limiting examples, as well as memory circuits for commanding acquisition of sensed signals from the x-ray detector 222. IDC 234 is coupled via two-way fiber optic conductors to detector control circuitry 236 within the digital x-ray detector 222. In some examples, other communication systems and technologies may also be used, such as Ethernet communication protocols and wireless communication devices and protocols. IDC 234 thereby exchanges command signals for image data within the digital x-ray detector 222 during operation.

Detector control circuitry 236 receives DC power from a power source 238. Detector control circuitry 236 is configured to originate timing and control commands for row and column electronics used to acquire image data during data acquisition phases of operation of the system. Detector control circuitry 236 therefore transmits power and control signals to reference/regulator circuitry 240, and receives digital image pixel data from the reference/regulator circuitry 240.

In some examples, the detector control circuitry 236 comprises a processor and a non-transitory memory configured with a neural network model as well as with executable instructions for training the neural network model to remove or reduce EMI noise and RCN from digital image pixel data received from the reference/regulatory circuitry 240. Such a neural network model is described further herein with regard to FIGS. 3 and 4.

In one example, the digital x-ray detector 222 comprises a scintillator that converts x-ray photons received on the detector surface during examinations into lower energy (light) photons. An array of photodetectors then converts the light photons to electrical signals, which are representative of the number of photons or the intensity of radiation impacting individual pixel regions of the detector surface. In some examples, the x-ray photons may be directly converted to electrical signals.

Readout electronics convert the resulting analog signals to digital values that can be processed, stored, and displayed, such as in a display device 195 following reconstruction of the image. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics as described below. The drains of the transistors in a column are connected together and the electrode of each column is connected to an individual channel of the readout electronics.

In the particular example depicted in FIG. 2, by way of example, a row bus 242 includes a plurality of conductors for enabling readout from various rows of the digital x-ray detector 222, as well as for disabling rows and applying a charge compensation voltage to selected rows, where desired. A column bus 244 includes additional conductors for commanding readout from the columns while the rows are sequentially enabled. Row bus 242 is coupled to a series of row drivers 246, each of which commands enabling a series of rows in the digital x-ray detector 222. Similarly, readout electronics 248 are coupled to column bus 244 for commanding readout of all columns of the digital x-ray detector 222.

In the illustrated example, row drivers 246 and readout electronics 248 are coupled to a detector panel 250, which may be subdivided into a plurality of sections 252. Each section 252 is coupled to one of the row drivers 246, and includes a number of rows. Similarly, each column driver 248 is coupled to a series of columns. The photodiode and thin film transistor arrangement mentioned above thereby defines a series of pixels or discrete picture elements 254 which are arranged in rows 256 and columns 258. The rows and columns define an image matrix 260, having a height 262 and a width 264.

Each pixel 254 is generally defined at a row and column crossing, at which a column electrode 268 crosses a row electrode 270. As mentioned above, a thin film transistor 272 is provided at each crossing location for each pixel, as is a photodiode 274. As row drivers 246 enable each row, signals from each photodiode 274 may be accessed via readout electronics 248, and converted to digital signals for subsequent processing and image reconstruction. Thus, an entire row of pixels is controlled simultaneously when the scan line attached to the gates of all the transistors of pixels on that row is activated. Consequently, each of the pixels in that particular row is connected to a data line, through a switch, which is used by the readout electronics to restore the charge to the photodiode 274.

It should be noted that in certain systems, as each of the associated dedicated readout channels restores the charge to all the pixels in a row simultaneously, the readout electronics is converting the measurements from the previous row from an analog voltage to a digital value. Furthermore, the readout electronics may transfer the digital values from rows before the acquisition subsystem, which will perform some processing prior to displaying a diagnostic image on a monitor or writing it to film.

The circuitry used to enable the rows may be referred to as row enable or field effect transistor (FET) circuitry based upon the use of field effect transistors for such enablement (row driving). The FETs associated with the row enable circuitry described above are placed in an "on" or conducting state for enabling the rows, and are turned "off" or placed in a non-conducting state when the rows are not enabled for readout. Despite such language, it should be appreciated that the particular circuit components used for the row drivers and column readout electronics may vary, and the present disclosure is not limited to the use of FETs or any particular circuit components.

Electrical magnetic interference (EMI) is added to, or more generally affects the x-ray image data through the detector panel and readout circuits described hereinabove. In particular, the pixels on the panel are arranged as a two-dimensional matrix with one column being read by means of a specific readout circuit via a data line. The scan lines control the order and time instant of the readout of a pixel. The pixels on a row of the panel are connected by one scan line so that each row is read out at the same time. As a result, the additive interference appears as a row-correlated noise (RCN) type of artifact that is seen as lines or bands in the row direction of the image.

Such EMI noise and RCN artifacts are a common issue for digital x-ray detectors. In particular, the sensitivity of digital x-ray detectors such as the digital x-ray detector 222 is often increased in order to enable reduced x-ray dose for patients. However, by increasing the sensitivity, an increased number of scan lines or rows results in an increased amount of electromagnetic interference and thus a large amount of noise on the scan lines. The noise frequency is usually associated with the row spatial distribution and external electromagnetic sources. Typical approaches to reducing EMI noise and RCN artifacts include providing physical shielding for electromagnetic sources in x-ray imaging systems to reduce the electromagnetic interference. As described further herein, a well-trained neural network model is configured to remove or reduce EMI noise and RCN artifacts in acquired images in real-time in the digital x-ray detector.

As an illustrative example, FIG. 3 shows a high-level diagram illustrating an example method 300 for reducing image noise with a neural network model 320 according to an embodiment. The neural network model 320 may be implemented in the x-ray detector 134 of the x-ray imaging system 100. For example, the neural network model 320 may be implemented in the detector control circuitry 236 of the digital x-ray detector 222 and may be configured to perform EMI noise and RCN cancellation in real-time as image data is acquired by the digital x-ray detector 222. In other examples, the neural network model 320 may be implemented as a neural network model in the non-transitory memory 182 of an operation console 180 of an x-ray imaging system 100, so that the neural network model 320 may be used to remove or reduce image noise after the image data is received from the x-ray detector 134.

A noisy image 305 is acquired via a digital x-ray detector such as the digital x-ray detector 222 described hereinabove. The noisy image 305 comprises an image acquired with the digital x-ray detector that includes EMI noise and/or RCN as described hereinabove. The noisy image 305 is sub-divided 307 into a plurality of noisy sub-images 310 including a first noisy sub-image 311, a second noisy sub-image 312, a third noisy sub-image 313, and a fourth noisy sub-image 314. In particular, the noisy image 305 is sub-divided 307 or cut in a direction parallel to the data line and perpendicular to the scan line, as depicted. The noisy image 305 may be sub-divided 307 into four noisy sub-images 310, as depicted, though it should be appreciated that the noisy image 305 may be sub-divided 307 into a different number of sub-images 310 in other examples without departing from the scope of the present disclosure.

The neural network model 320 includes an input layer 321 and an output layer 329, as well as a plurality of hidden layers therebetween. In some examples, the neural network model 320 includes a first layer 323, a second layer 325, and a third layer 327. The first layer 323 and the second layer 325 may comprise non-linear layers while the third layer 327 may comprise a linear layer. It should be appreciated that such an architecture of two non-linear layers followed by a linear layer allows the neural network model to be trained quickly while providing robust performance.

Each noisy sub-image of the plurality of noise sub-images 310 is input separately to the neural network model 320. For example, the first noisy sub-image 311 is input to the input layer 321 of the neural network model 320. The output of the input layer 321 is then input to the first layer 323, the output of the first layer 323 is input to the second layer 325, the output of the second layer 325 is input to the third layer 327, and the output of the third layer 327 is output by the output layer 329 as a first corrected sub-image 341.

The second noisy sub-image 312 is similarly input to and processed by the neural network model 320 to generate the second corrected sub-image 342, the third noisy sub-image 313 is input to and processed by the neural network model 320 to generate the third corrected sub-image 343, and the fourth noisy sub-image 314 is input to and processed by the neural network model 320 to generate the fourth corrected sub-image 344. Thus, the plurality of noisy sub-images 310 are separately input to the neural network model 320 to obtain the plurality of corrected sub-images 340.

After obtaining the plurality of corrected sub-images 340, the plurality of corrected sub-images 340 are combined 347 into a corrected image 350. The corrected image 350 corresponds to the original noisy image 305 with a reduced amount of EMI noise and RCN.

To further illustrate how the neural network model 320 may effectively reduce EMI noise artifacts and RCN artifacts, FIG. 4 shows a high-level diagram illustrating an example architecture for a neural network model 400 according to an embodiment. The neural network model 400 may be implemented as the neural network model 320 depicted in FIG. 3, as an illustrative and non-limiting example. As depicted, the neural network model 400 comprises an input layer 405, a first layer 410, a second layer 430, a third layer 450, and an output layer 475.

The input layer 405 with a size equal to the number of elements R in the input vector 407 denoted also by p. As mentioned hereinabove, the input layer 405 and thus the input vector 407 comprise a sub-image, such as one of the sub-images 311, 312, 313, and 314. While the sub-images 311, 312, 313, and 314 are two-dimensional images and thus comprise a two-dimensional array or matrix of pixels, the two-dimensional array forming the sub-images may be reduced or concatenated into a one-dimensional vector to form the input vector 407. For example, the columns of the two-dimensional array corresponding to the first sub-image 311 may be concatenated to form the input vector 407 when processing the first sub-image 311 with the neural network model 400. However, while the architecture of the neural network model 400 is described herein with regard to a one-dimensional input vector 407, it should also be appreciated that the sub-images 310 may be input as two-dimensional arrays, and so the corresponding size of the components described herein below may be adjusted accordingly without departing from the scope of the present disclosure.

The input vector 407 is input to the first layer 410 and is multiplied by the first weight vector 412 of the first layer 410. The first weight vector 412 is given by $LW_{1,1}$ where L is the identity matrix and W is the matrix of weights, and the result of the multiplication of the input vector 407 with the first weight vector 412 has a size equal to the product of the number of neurons $S_1$ and the number of elements R in the input vector 407.

In addition to the first weight vector 412, the first layer 410 further includes a first bias vector 416 denoted by $b_1$ with a size equal to the number of neurons $S_1$ in the first layer 410. The first bias vector 416 is multiplied by a scaling factor 415 set to unity or one. The result of multiplying the input vector 407 with the first weight vector 412 is summed with the first bias vector 416 at the first summing junction 420 of the first layer 410 to obtain the first sum 422 denoted as $n_1$ with a size $S_1$ times one.

The first sum vector 422 is the argument of the first transfer function 425 denoted as $f_1$ which results in a first output vector 427 of the first layer 410 denoted as $a_1$ with a size $S_1$. The first output vector 427 of the first layer 410 may thus be expressed as:

$$a_1 = f_1(LW_{1,1}p + b_1).$$

The first output vector 427 from first layer 410 is input to the second layer 430 and is multiplied by the second weight vector 432 of the second layer 430. The second weight vector 432 is given by $LW_{2,1}$ where L is the identity matrix and W is the matrix of weights, and the result of the multiplication of the first output vector 427 with the second weight vector 432 has a size equal to the product of the number of neurons $S_1$ in the first layer 410 and the number of neurons $S_2$ in the second layer 430.

In addition to the second weight vector 432, the second layer 430 further includes a second bias vector 436 denoted by $b_2$ with a size equal to the number of neurons $S_2$ in the second layer 430. The second bias vector 436 is multiplied by a scaling factor 435 initially set to unity or one. The result of multiplying the first output vector 427 with the second weight vector 432 is summed with the second bias vector 436 at the second summing junction 440 of the second layer 430 to obtain the second sum vector 442 denoted as $n_2$ with a size $S_2$ times one.

The second sum vector 422 is the argument of the second transfer function 445 denoted as $f_2$ which results in a second output 447 of the second layer 430 denoted as $a_2$ with a size $S_2$. The second output vector 447 of the second layer 430 may thus be expressed as:

$$a_2 = f_2(LW_{2,1}a_1 + b_2).$$

The second output vector 447 from second layer 430 is input to the third layer 450 and is multiplied by the third weight vector 452 of the third layer 450. The third weight vector 452 is given by $LW_{3,1}$ where L is the identity matrix and W is the matrix of weights, and the result of the multiplication of the second output vector 447 with the third weight vector 452 has a size equal to the product of the number of neurons $S_2$ in the second layer 430 and the number of neurons $S_3$ in the third layer 450.

In addition to the third weight vector 452, the third layer 450 further includes a third bias vector 456 denoted by $b_3$ with a size equal to the number of neurons $S_3$ in the third layer 450. The third bias vector 456 is multiplied by a scaling factor 455 initially set to unity or one. The result of multiplying the second output vector 447 with the third weight vector 452 is summed with the third bias vector 456 at the third summing junction 460 of the third layer 450 to obtain the third sum vector 462 denoted as $n_3$ with a size $S_3$ times one.

The third sum vector 462 is the argument of the third transfer function 465 denoted as $f_3$ which results in a third output 467 of the third layer 450 denoted as $a_3$ with a size $S_3$. The third output vector 467 of the third layer 450 may thus be expressed as:

$$a_3 = f_3(LW_{3,1}a_2 + b_3).$$

The third output vector 467 of the third layer 450 is provided to the output layer 475 which has a size equal to the number of neurons $S_3$ in the third layer 450. The output layer 475 may thus be expressed in terms of the weights and biases of the layers as well as the input vector p:

$$y = a_3 = f_3(LW_{3,1}f_2(LW_{2,1}f_1(LW_{1,1}p + b_1) + b_2) + b_3).$$

The first transfer function $f_1$ and the second transfer function $f_2$ may comprise non-linear transfer functions while the third transfer function $f_3$ may comprise a linear transfer function.

Thus the neural network model 320 may be configured as the neural network model 400 for reducing or cancelling row-correlated noise artifacts in acquired images. Further, in some examples, the neural network model 400 may include one or more noise filters such as a filter 482 and a filter 484. The filters 482 and 484 may comprise bandpass filters, for example, with a frequency band centered on noise frequencies caused by electromagnetic interference endemic to digital x-ray detectors such as the digital x-ray detector 222. For example, if the noise frequency is one Hertz, the filters 482 and 484 may provide a noise reduction filter around this noise frequency. The filters 482 and 484 may be positioned to filter the first output vector 427 and the second output vector 447, respectively, as an illustrative and non-limiting example.

Figure 5:
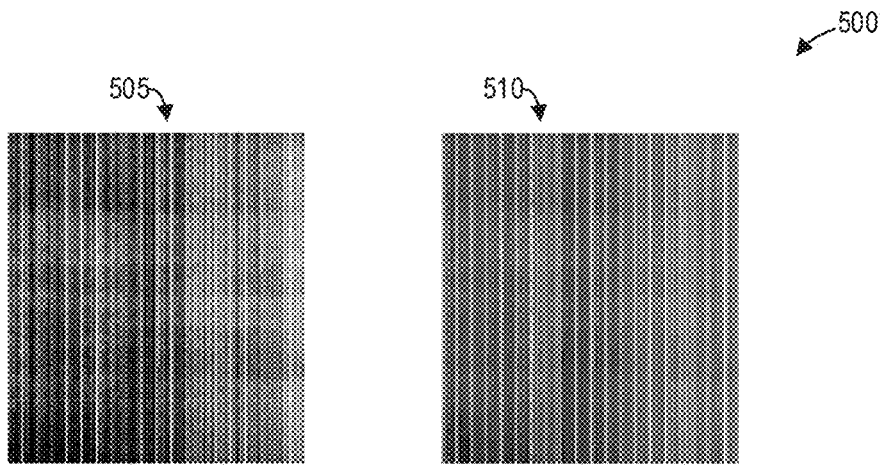
FIG. 5 shows a pair of example images including a noisy image and a clean image for training a neural network model to reduce image noise according to an embodiment.
Figure 6:
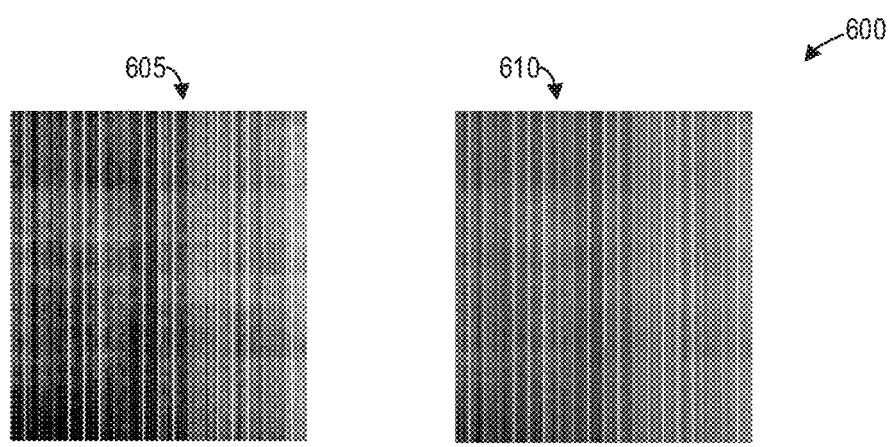
FIG. 6 shows a pair of example images including an acquired image and the acquired image after correction with a trained neural network model according to an embodiment.

FIG. 5 shows a pair of example images 500 including a noisy image 505 and a clean image 510 for training a neural network model to reduce image noise according to an embodiment. The row-correlated noise of the noisy image 505 is above 60% while the row-correlated noise of the clean image 510 is approximately 2%. The noisy image 505 may be divided or sub-divided in a direction parallel to the data line to create a plurality of noisy sub-images. The clean image 510 may be similarly divided in the direction parallel to the data line to create a plurality of clean sub-images. The plurality of noisy sub-images and the plurality of clean sub-images may then be used to train a neural network model such as the neural network model 320 or 400 described hereinabove. During training of the neural network model, an optimized set of weights and biases are determined to best fit the target of the plurality of clean sub-images from the input of the plurality of noisy sub-images.

In some examples, the neural network model may be trained using batch training, in which the weights and biases are only updated after all of the plurality of noisy sub-images are input and then the output is compared to the corresponding plurality of clean sub-images. In other examples, the neural network model may be trained using incremental training, wherein the gradient is computed and the weights and biases are updated after each noisy sub-image is input to the neural network model.

Thus, to train the neural network, the clean image 510 or a clean sub-image of the clean image 510 is designated as an ideal target t while the corresponding noisy image 505 or a noisy sub-image of the noisy image 505 is designated as the input p for the neural network model. Each pixel of the ideal target t may thus be considered to be paired with a corresponding pixel of the input p:

$$\{p_1,t_1\},\{p_2,t_2\},\ldots,\{p_R,t_R\},$$

where R is the number of pixels in each image or sub-image. Further, to train the neural network model, a goal for the converging criterion is set. For example, a target mean squared error (MSE) may be established, wherein the MSE is given by:

$$MSE = \frac{1}{R}\sum_{k=1}^{R} e(k)^2 = \frac{1}{R}\sum_{k=1}^{R} [t(k) - a(k)]^2,$$

where t is the target image and a is the network output, as discussed hereinabove. Thus, the MSE may be calculated for each pass of the training (i.e., each traverse through all of the training input and the target vector). Further, backpropagation may be used for determining updated weights and biases for the neurons of the neural network model. For example, for backpropagation training, the Widow-Hoff learning rule may be generalized to multiple-layer networks and non-linear differentiable transfer functions, so that:

$$x(k+1)=x(k)-\alpha(k)g(k),$$

wherein:

$$x(k)=w(k)\cup b(k)$$

is a vector of current weights and biases, g(k) is the current gradient, and α(k) is the learning rate.

After training the neural network model such as the neural network model 320 or the neural network model 400, the trained neural network model may accept a noisy image as input and output a corrected image with reduced RCN and/or reduced EMI noise. As an illustrative example, FIG. 6 shows a pair of example images 600 including an acquired image 605 and a corrected image 610 corresponding to the acquired image after correction with a trained neural network model according to an embodiment. That is, a neural network model configured as described hereinabove with regard to FIGS. 3 and 4 is trained with training data such as the noisy image 505 and the clean image 510, and the acquired image 605 is provided as input to the trained neural network model.

In particular, the neural network model is trained with a goal MSE of 5%, a learning rate a of 0.01, with a conjugate gradient search direction and a golden section search method. The acquired image 605 is sub-divided into a plurality of sub-images which are provided as input to the trained neural network model, and the corrected sub-images output by the trained neural network model are stitched together to form the corrected image 610. The RCN of the acquired image 605 is 62.75% while the RCN of the corrected image 610 is 12.28%. Thus, the trained neural network model substantially removes the RCN while preserving image textures, as depicted.

Figure 7:
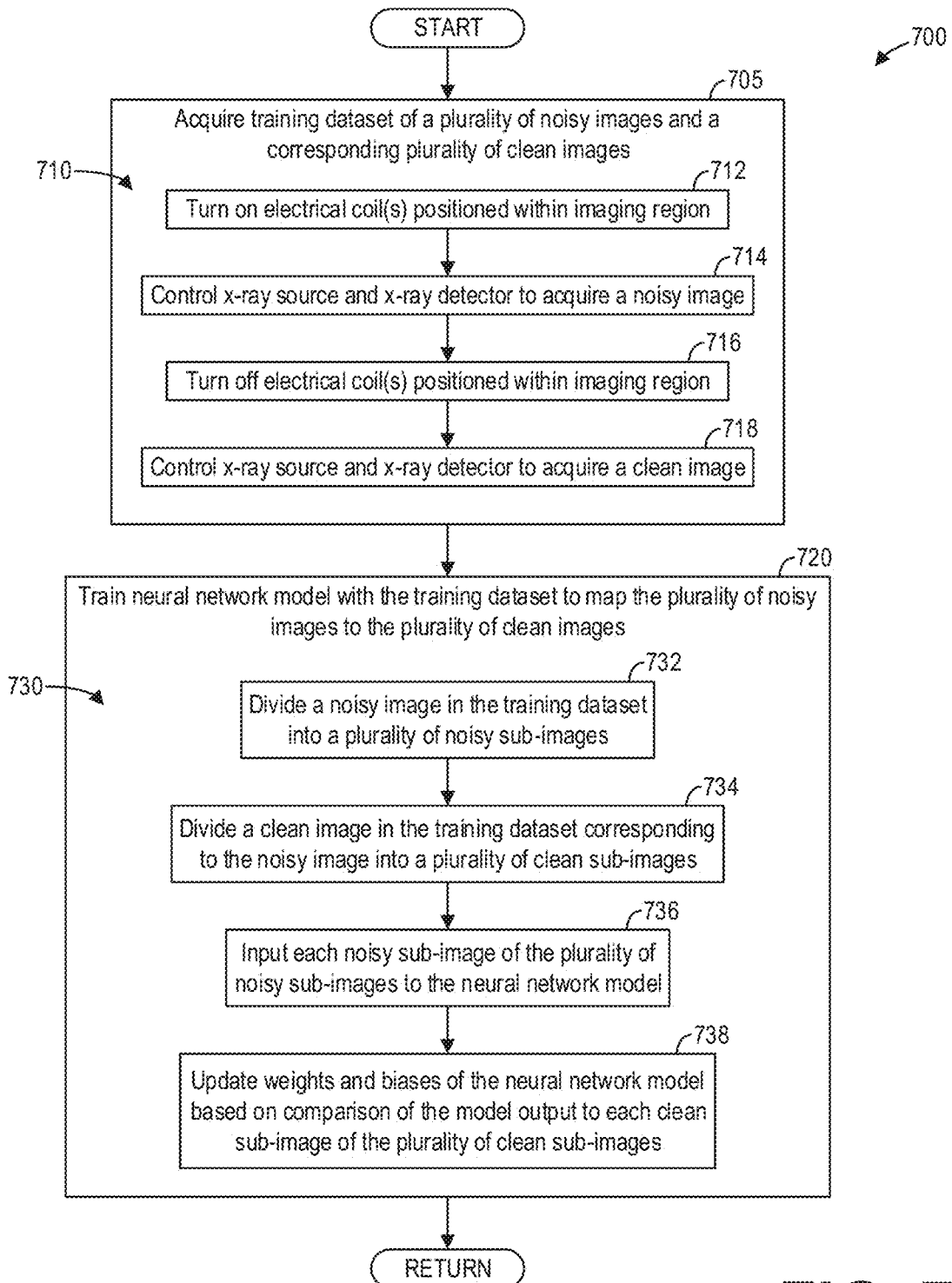
FIG. 7 shows a high-level flow chart illustrating an example method for training a neural network model to reduce image noise according to an embodiment.
Figure 8:
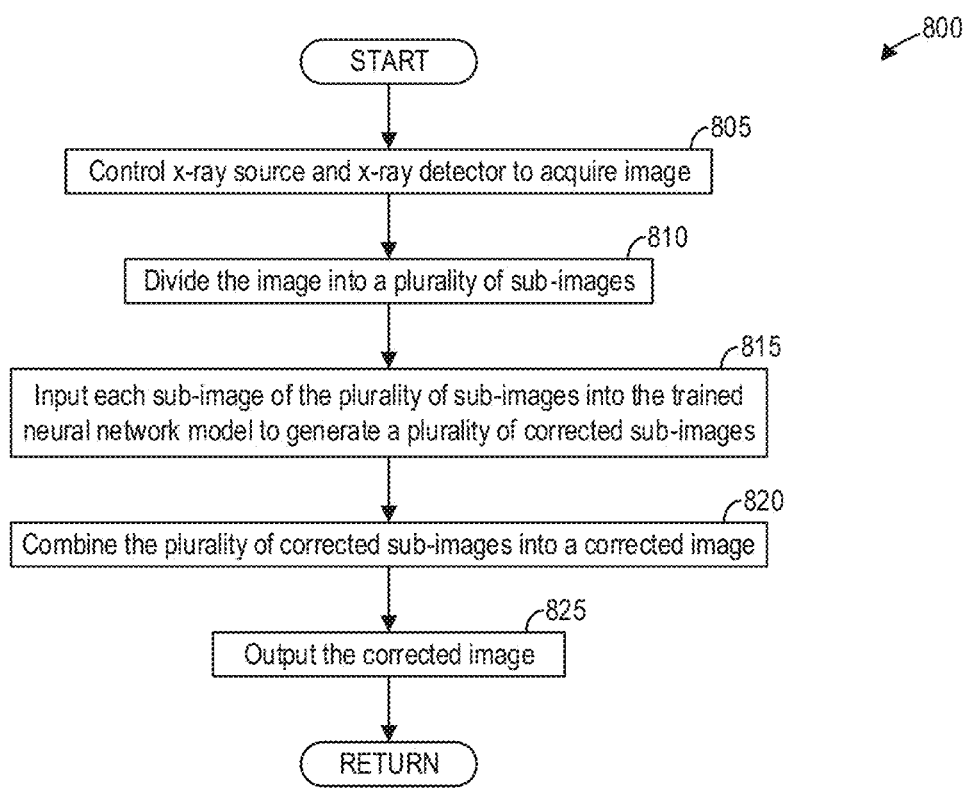
FIG. 8 shows a high-level flow chart illustrating an example method for correcting an acquired image with a neural network model according to an embodiment.

FIG. 7 shows a high-level flow chart illustrating an example method 700 for training a neural network model to reduce image noise according to an embodiment. In particular, method 700 relates to training a neural network model, such as the neural network model 320 or 400 described hereinabove, to reduce EMI noise and RCN in images acquired with a digital x-ray detector, such as the digital x-ray detector 134 or 222 described hereinabove. Method 700 is described with regard to the systems and components of FIGS. 1-4, though it should be appreciated that the method 700 may be implemented with other systems and components without departing from the scope of the present disclosure. Method 700 may be configured as instructions 188 stored in the non-transitory memory 182 and executable by the processor 181 of the x-ray imaging system 100, for example.

Method 700 begins at 705. At 705, method 700 acquires a training dataset comprising a plurality of noisy images and a corresponding plurality of clean images. The training dataset is intended for training a neural network model, such as the neural network model 320 or 400, to generate noise-reduced images from acquired x-ray images. To train the neural network model to reduce or eliminate particular types of image noise, the training dataset should include noisy images exhibiting the particular types of image noise as well as corresponding target or clean images that do not exhibit the particular types of image noise. For example, to reduce EMI noise and row-correlated noise, the noisy images should exhibit EMI noise and/or row-correlated noise. Further, it should be appreciated that a larger training dataset results in an improved performance of the neural network model.

As depicted, method 700 includes a sub-routine 710 for acquiring the training dataset. The sub-routine 710 relates to acquiring a noisy image and a corresponding clean image, according to some examples. The sub-routine 710 of method 700 begins at 712, wherein method 700 turns on one or more electrical coils positioned within the imaging region or adjacent to the imaging region. Continuing at 714, method 700 controls the x-ray source and the x-ray detector, such as the x-ray source 111 and the x-ray detector 134, to acquire a noisy image while the electrical coil(s) are turned on. That is, method 700 controls the x-ray source to generate a beam of x-rays directed toward the x-ray detector, and further controls the x-ray detector to generate image data from the detected x-rays impinging the surface of the detector. The electromagnetic fields generated by the one or more electrical coils cause electromagnetic interference at the x-ray detector as discussed hereinabove, which thereby results in substantial EMI noise artifacts and RCN artifacts in the acquired image. At 716, method 700 turns off the electrical coil(s) positioned within or adjacent to the imaging region. At 718, method 700 controls the x-ray source and the x-ray detector to acquire a clean image. Method 700 may control the x-ray source and the x-ray detector exactly as controlled at 714 in order to provide consistency between the acquired images. Further, as the electrical coil(s) are turned off and thus as the electromagnetic interference at the x-ray detector is reduced, the image acquired via the x-ray detector at 718 exhibits substantially fewer EMI noise artifacts and RCN artifacts. Thus, as the primary difference between the acquisition of the image at 714 and the acquisition of the image at 718 is the presence of intentional EMI, the clean image acquired at 718 may be considered a target image for training the neural network model with the noisy image acquired at 714 as input.

As the sub-routine 710 relates to acquiring a single pair of images for training the neural network model, method 700 may repeat the sub-routine 710 to generate a plurality of image pairs for the training dataset. In some examples, variations may be applied in order to obtain a variety of samples. For example, the one or more electrical coils may be selectively powered on with different amounts of current in order to produce different electromagnetic interference at the x-ray detector when acquiring the noisy images. Similarly, the x-ray source may be controlled with different tube currents and/or tube voltages during different iterations of the sub-routine 710 to further expand the variety of samples in the training dataset.

After acquiring the training dataset at 705, method 700 continues to 720. At 720, method 700 trains the neural network model with the training dataset to map the plurality of noisy images to the plurality of clean images. As mentioned hereinabove, the neural network model may comprise the neural network model 320 or 400. If the training dataset includes a large variety of samples with different amounts of EMI and varying x-ray energy levels and intensities, the neural network model trained on the training dataset may exhibit robust performance when correcting x-ray images with image noise artifacts.

In order to train the neural network model on the entire training dataset, method 700 may include a sub-routine 730 that may be repeatedly executed during the training of the neural network model. The sub-routine 730 of method 700 begins at 732. At 732, method 700 divides a noisy image in the training dataset into a plurality of noisy sub-images. Dividing the noisy image into a plurality of noisy sub-images increases the training base and also shortens the training time. Further, the noisy image may be divided or sub-divided into a plurality of sub-images in a direction parallel to the data line and perpendicular to the scan line. Selecting the sub-images perpendicular to the scan lines provides improved noise reduction and faster converging of the neural network model in comparison to sub-images that are parallel to the scan lines. Continuing at 734, method 700 also divides a clean image in the training dataset corresponding to the noisy image into a plurality of clean sub-images. Method 700 divides the clean image similarly to how the noisy image is divided at 732. That is, the clean image is divided in the direction parallel to the data line and perpendicular to the scan line, and furthermore is divided such that the size of each clean sub-image is equivalent and equal to the size of each noisy sub-image. At 736, method 700 inputs each noisy sub-image of the plurality of noisy sub-images to the neural network model to obtain the model output. At 738, method 700 updates the weights and biases of the layers of the neural network model based on a comparison of the model output to each clean sub-image of the plurality of clean sub-images. For example, method 700 may use the backpropagation technique to update the weights to minimize the loss function. A conjugate gradient method may be used to produce faster convergence during backpropagation, in comparison to adjusting weights in the steepest descent direction. The weights and biases may be updated in a batch, where weights and biases are updated after all of the noisy sub-images and clean sub-images of the noisy image and the clean image are presented to the neural network model as inputs and targets. Alternatively, the gradient may be computed and the weights and biases updated after each noisy sub-image is applied to the neural network model.

Sub-routine 730 returns after updating the weights and biases of the neural network model. As sub-routine 730 relates to training the neural network model on a single noisy image and its corresponding clean or target image, method 700 may repeatedly execute the sub-routine 730 for each image pair in the training dataset. The weights and biases determined during an iteration of the sub-routine 730 are maintained and then updated further during the next iteration of the sub-routine 730, such that the neural network model is eventually trained on the entire training dataset. Once the neural network model is trained, method 700 returns.

Once the trained neural network model is validated and testing tested, the trained neural network model may be deployed for reducing image noise in images acquired with an x-ray imaging system, such as the x-ray imaging system 100. As an illustrative example, FIG. 8 shows a high-level flow chart illustrating an example method 800 for correcting an acquired image with a neural network model according to an embodiment. In particular, method 800 relates to using the neural network model described herein, such as the neural network model 320 or 400, after training the neural network model as described hereinabove with regard to FIG. 7. Method 800 is described with regard to the systems and components of FIGS. 1-4, though it should be appreciated that the method 800 may be implemented with other systems and components without departing from the scope of the present disclosure. In some examples, the neural network model may be implemented in the digital x-ray detector 222, for example, such that the image correction occurs at the digital x-ray detector 222 or at the x-ray detector 134. In other examples, the neural network model may be implemented in a computing system such as the image processor 192, for example, or via the processor 181 and memory 182 of the operation console 180, for reducing the image noise after transmission of the image data from the x-ray detector 134 to the operation console 180. Method 800 may be implemented as instructions 188 in the non-transitory memory 182 and executable by the processor 181, or may be implemented as instructions distributed between the memory 182 and a memory of the x-ray detector 134 or the digital x-ray detector 222, in some examples.

Method 800 begins at 805. At 805, method 800 controls the x-ray source and the x-ray detector to acquire an image. For example, method 800 controls the x-ray source to generate a beam of x-rays toward the x-ray detector, and controls the x-ray detector to convert the detected x-rays into electrical signals and then into digital signals corresponding to image data. An imaging subject, such as a patient in a medical diagnostic application or an inanimate object, for example, may be positioned between the x-ray source and the x-ray detector such that the imaging subject attenuates the beam of x-rays. The resulting image data thus forms an image of the internal structure of the imaging subject.

After acquiring the image, method 800 continues to 810. At 810, method 800 divides the image into a plurality of sub-images. Method 800 divides the image along the direction parallel to the data line and perpendicular to the scan line, as discussed hereinabove. Furthermore, method 800 divides the image according to how the neural network model is structured and trained. For example, method 800 divides the image into the sub-images such that each sub-image is appropriately sized for the input layer of the neural network model.

Continuing at 815, method 800 inputs each sub-image of the plurality of sub-images into the trained neural network model to generate a plurality of corrected sub-images. At 820, method 800 combines the plurality of corrected sub-images into a corrected image. That is, the plurality of corrected sub-images are positioned adjacent to each other in an appropriate order according to how the original acquired image was divided. Then, at 825, method 800 outputs the corrected image. For example, if the trained neural network model is implemented in the digital x-ray detector 222 at the detector control circuitry 236, the corrected image may be output to the x-ray data acquisition unit 191 for optional image post-processing. Additionally, the corrected image may be output, for example, to the display device 195 or to memory 182 for subsequent retrieval or additional processing. As the corrected image is generated by the trained neural network model, the corrected image output at 825 exhibits significantly fewer EMI noise artifacts and RCN artifacts relative to the image acquired at 805. After outputting the corrected image, method 800 returns.

A technical effect of the present disclosure includes the reduction of row-correlated noise artifacts in acquired images. Another technical effect of the present disclosure includes the improvement of image quality in images acquired with sensitive digital x-ray detectors without the need for extensive electromagnetic shielding. Yet another technical effect of the disclosure includes the dividing or splitting of acquired images into sub-images in a particular direction. Another technical effect of the disclosure includes the improved performance and faster converging time of a neural network model for reducing noise artifacts in images.

Thus, in one embodiment, a method for an x-ray imaging system comprises acquiring, with an x-ray detector, an image including a noise artifact caused by electromagnetic interference, inputting the image to a trained neural network model to obtain a corrected image with the noise artifact substantially removed, and outputting the corrected image.

In a first example of the method, pixels are arranged in rows in the x-ray detector with pixels in a row connected by a scan line, and acquiring the image with the x-ray detector comprises reading out the pixels in the row at a same time via the scan line. In a second example of the method optionally including the first example, the method further comprises dividing the image into sub-images, wherein inputting the image to the trained neural network model comprises inputting each sub-image of the sub-images to the trained neural network model. In a third example of the method optionally including one or more of the first and second examples, the trained neural network model outputs corrected sub-images, and obtaining the corrected image with the noise artifact substantially removed comprises combining the corrected sub-images output by the trained neural network model into the corrected image. In a fourth example of the method optionally including one or more of the first through third examples, the noise artifact comprises row-correlated noise, and dividing the image into the sub-images comprises dividing the image along a direction perpendicular to the scan line. In a fifth example of the method optionally including one or more of the first through fourth examples, the trained neural network model is implemented in circuitry of the x-ray detector, and outputting the corrected image comprises transmitting the corrected image from the x-ray detector to an operation console of the x-ray imaging system. In a sixth example of the method optionally including one or more of the first through fifth examples, the method further comprises transmitting the image from the x-ray detector to an operation console of the x-ray imaging system, wherein the trained neural network model is implemented in the operation console, and wherein outputting the corrected image comprises outputting the image to a display device communicatively coupled to the operation console for display. In a seventh example of the method optionally including one or more of the first through sixth examples, the trained neural network model comprises two non-linear layers and a linear layer. In an eighth example of the method optionally including one or more of the first through seventh examples, the method further comprises acquiring a noisy image with the x-ray detector while an electromagnetic coil positioned near the x-ray detector is activated, acquiring a clean image with the x-ray detector while the electromagnetic coil is deactivated, and training the trained neural network model by using the noisy image as an input and the clean image as a target. In a ninth example of the method optionally including one or more of the first through eighth examples, the method further comprises applying a noise filter to convolved output of the non-linear layers.

In another embodiment, a method comprises acquiring, with an x-ray detector, an image including a noise artifact, dividing the image into a plurality of sub-images, inputting each sub-image of the plurality of sub-images into a trained neural network model to generate a plurality of corrected sub-images, combining the plurality of corrected sub-images into a corrected image, and outputting the corrected image.

In a first example of the method, pixels are arranged in rows in a panel of the x-ray detector with pixels in a row connected by a scan line, and acquiring the image with the x-ray detector comprises reading out the pixels in the row at a same time via the scan line. In a second example of the method optionally including the first example, the noise artifact comprises row-correlated noise, and dividing the image into the sub-images comprises dividing the image along a direction perpendicular to the scan line. In a third example of the method optionally including one or more of the first and second examples, the method further comprises acquiring a plurality of noisy images with the x-ray detector while an electromagnetic coil positioned near the x-ray detector is activated, acquiring a plurality of clean images with the x-ray detector while the electromagnetic coil is deactivated, and training the trained neural network model by using the plurality of noisy images as inputs and the plurality of clean images as targets.

In yet another embodiment, a system comprises an x-ray source configured to generate a beam of x-rays, an x-ray detector configured to detect the beam of x-rays, and a processor configured with instructions in non-transitory memory that when executed cause the processor to acquire, with the x-ray detector, an image including a noise artifact caused by electromagnetic interference, input the image to a trained neural network model to obtain a corrected image with the noise artifact substantially removed, and output the corrected image.

In a first example of the system, the x-ray detector comprises a detector panel configured with a plurality of pixels arranged in plurality of rows, wherein pixels in a row are connected by a scan line, and wherein acquiring the image with the x-ray detector comprises reading out the pixels in the row at a same time via the scan line. In a second example of the system optionally including the first example, the processor is further configured with instructions that when executed cause the processor to divide the image into sub-images, wherein inputting the image to the trained neural network model comprises inputting each sub-image of the sub-images to the trained neural network model. In a third example of the system optionally including one or more of the first and second examples, the trained neural network model outputs corrected sub-images, and the processor is further configured with instructions that when executed cause the processor to combine the corrected sub-images output by the trained neural network model to generate the corrected image. In a fourth example of the system optionally including one or more of the first through third examples, the noise artifact comprises row-correlated noise, and dividing the image into the sub-images comprises dividing the image along a direction perpendicular to the scan line. In a fifth example of the system optionally including one or more of the first through fourth examples, the processor and the trained neural network are integrated into the x-ray detector.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for an x-ray imaging system, comprising:
   acquiring, with an x-ray detector, an image including a noise artifact caused by electromagnetic interference;
   inputting the image to a trained neural network model to obtain a corrected image with reduced noise artifact;
   outputting the corrected image;
   wherein the method further comprises:
      dividing the image into sub-images, wherein inputting the image to the trained neural network model comprises inputting each sub-image of the sub-images to the trained neural network model;
      acquiring a noisy image with the x-ray detector while an electromagnetic coil positioned near the x-ray detector is activated, acquiring a clean image with the x-ray detector while the electromagnetic coil is deactivated, and training the trained neural network model by using the noisy image as an input and the clean image as a target; and
   wherein the trained neural network model outputs corrected sub-images, and wherein obtaining the corrected image with the reduced noise artifact comprises combining the corrected sub-images output by the trained neural network model into the corrected image.

2. The method of claim 1, wherein pixels are arranged in rows in the x-ray detector with pixels in a row connected by a scan line, and wherein acquiring the image with the x-ray detector comprises reading out the pixels in the row at a same time via the scan line.

3. The method of claim 1, wherein the noise artifact comprises row-correlated noise, and wherein dividing the image into the sub-images comprises dividing the image along a direction perpendicular to the scan line.

4. The method of claim 1, wherein the trained neural network model is implemented in circuitry of the x-ray detector, and wherein outputting the corrected image comprises transmitting the corrected image from the x-ray detector to an operation console of the x-ray imaging system.

5. The method of claim 1, further comprising transmitting the image from the x-ray detector to an operation console of the x-ray imaging system, wherein the trained neural network model is implemented in the operation console, and wherein outputting the corrected image comprises outputting the image to a display device communicatively coupled to the operation console for display.

6. The method of claim 1, wherein the trained neural network model comprises two non-linear layers and a linear layer.

7. The method of claim 6, further comprising applying a noise filter to convolved output of the non-linear layers.

8. The method of claim 1, wherein the neural network model is trained using incremental training, wherein weights and biases of the neural network model are updated after each noisy sub-image is input to the neural network model.

9. The method of claim 1, wherein the neural network model is trained using batch training, wherein weights and biases of the neural network model are updated after all the noisy sub-images are input to the neural network model and the output of the neural network model is compared to the corresponding clean sub-images.

10. A method, comprising:
    acquiring, with an x-ray detector, an image including a noise artifact;
    dividing the image into a plurality of sub-images;
    inputting each sub-image of the plurality of sub-images into a trained neural network model, wherein the trained neural network generates a plurality of corrected sub-images;
    combining the plurality of corrected sub-images into a corrected image;
    outputting the corrected image; and
    acquiring a plurality of noisy images with the x-ray detector while an electromagnetic coil positioned near the x-ray detector is activated, acquiring a plurality of clean images with the x-ray detector while the electromagnetic coil is deactivated, and training the trained neural network model by using the plurality of noisy images as inputs and the plurality of clean images as targets.

11. The method of claim 10, wherein pixels are arranged in rows in a panel of the x-ray detector with pixels in a row connected by a scan line, and wherein acquiring the image with the x-ray detector comprises reading out the pixels in the row at a same time via the scan line.

12. The method of claim 11, wherein the noise artifact comprises row-correlated noise, and wherein dividing the image into the sub-images comprises dividing the image along a direction perpendicular to the scan line.

13. A system, comprising:
an x-ray source configured to generate a beam of x-rays;
an x-ray detector configured to detect the beam of x-rays; and
a processor configured with instructions in non-transitory memory that when executed cause the processor to:
acquire, with the x-ray detector, an image including a noise artifact caused by electromagnetic interference;
input the image to a trained neural network model to obtain a corrected image with reduced noise artifact;
output the corrected image;
wherein the processor is further configured with instructions that when executed cause the processor to:
divide the image into sub-images, wherein inputting the image to the trained neural network model comprises inputting each sub-image of the sub-images to the trained neural network model;
acquire a noisy image with the x-ray detector while an electromagnetic coil positioned near the x-ray detector is activated, acquire a clean image with the x-ray detector while the electromagnetic coil is deactivated, and train the trained neural network model by using the noisy image as an input and the clean image as a target; and
wherein the trained neural network model outputs corrected sub-images, and wherein the processor is further configured with instructions that when executed cause the processor to combine the corrected sub-images output by the trained neural network model to generate the corrected image.

14. The system of claim 13, wherein the x-ray detector comprises a detector panel configured with a plurality of pixels arranged in plurality of rows, wherein pixels in a row are connected by a scan line, and wherein acquiring the image with the x-ray detector comprises reading out the pixels in the row at a same time via the scan line.

15. The system of claim 13, wherein the noise artifact comprises row-correlated noise, and wherein dividing the image into the sub-images comprises dividing the image along a direction perpendicular to the scan line.

16. The system of claim 13, wherein the processor and the trained neural network are integrated into the x-ray detector.

* * * * *